United States Patent
Han et al.

(10) Patent No.: US 8,527,435 B1
(45) Date of Patent: Sep. 3, 2013

(54) SIGMA TUNING OF GAUSSIAN KERNELS: DETECTION OF ISCHEMIA FROM MAGNETOCARDIOGRAMS

(75) Inventors: Long Han, Baltimore, MD (US); Mark Embrechts, Clifton Park, NY (US); Boleslaw Szymanski, Newtonville, NY (US); Karsten Sternickel, Bonn (DE); Alexander Ross, Albany, NY (US)

(73) Assignee: CardioMag Imaging, Inc., Latham, NY (US)

( * ) Notice: Subject to any disclaimer, the term of this patent is extended or adjusted under 35 U.S.C. 154(b) by 214 days.

(21) Appl. No.: 13/181,734

(22) Filed: Jul. 13, 2011

Related U.S. Application Data

(63) Continuation-in-part of application No. 12/819,095, filed on Jun. 18, 2010, which is a continuation of application No. 10/561,285, filed as application No. PCT/US2004/021307 on Jul. 1, 2004, now Pat. No. 7,742,806.

(60) Provisional application No. 60/483,961, filed on Jul. 1, 2003, provisional application No. 61/393,915, filed on Jul. 13, 2010.

(51) Int. Cl.
G06F 15/18 (2006.01)
G06G 7/48 (2006.01)
A61B 5/04 (2006.01)

(52) U.S. Cl.
USPC .................... 706/12; 703/3; 703/11; 600/509

(58) Field of Classification Search
None
See application file for complete search history.

(56) References Cited

U.S. PATENT DOCUMENTS

2007/0167846 A1* 7/2007 Sternickel et al. ............ 600/509
2008/0163824 A1* 7/2008 Moser et al. .................. 119/174
2011/0047105 A1* 2/2011 Sternickel et al. ............. 706/12

OTHER PUBLICATIONS

Bennett, K. & Embrechts, M. (2003). An Optimization Perspective on Kernel Partial Least Squares Regression. In J. Suykens, G. Horvath, C. M. S. Basu, & J. Vandewalle (Ed.), Advances in Learning Theory: Methods, Models and Applications, vol. 190 of NATO Science III: Computer & Systems Sciences (pp. 227-250). Amsterdam: IOS Press.
Golbraikh, A. & Tropsha, A. (2002). Beware of q2!. Journal of Molecular Graphics and Modeling, 20, 267-276.
Bi, J., Bennett, K., Embrechts, M., Breneman, C., & Song, M. (2003). Dimensionality Reduction via Sparse Support Vector Machines. Journal of Machine Learning Research, 3, 1229-1243.

(Continued)

*Primary Examiner* — Alan Chen
(74) *Attorney, Agent, or Firm* — Jay R. Yablon

(57) ABSTRACT

A novel Levenberg-Marquardt like second-order algorithm for tuning the Parzen window σ in a Radial Basis Function (Gaussian) kernel. Each attribute has its own sigma parameter. The values of the optimized σ are then used as a gauge for variable selection. Kernel Partial Least Squares (K-PLS) model is applied to several benchmark data sets to estimate effectiveness of second-order sigma tuning procedure for an RBF kernel. The variable subset selection method based on these sigma values is then compared with different feature selection procedures such as random forests and sensitivity analysis. The sigma-tuned RBF kernel model outperforms K-PLS and SVM models with a single sigma value. K-PLS models also compare favorably with Least Squares Support Vector Machines (LS-SVM), epsilon-insensitive Support Vector Regression and traditional PLS. Sigma tuning and variable selection is applied to industrial magnetocardiograph data for detection of ischemic heart disease from measurement of magnetic field around the heart.

9 Claims, 4 Drawing Sheets

(56) References Cited

OTHER PUBLICATIONS

Blanchard, G., & Krämer, N. (2010). Kernel Partial Least Squares is Universally Consistent. Thirteenth International Conference on Artificial Intelligence and Statistics (AISTATS), Sardinia, Italy.

Blum, A. & Langley, P. (1997). Selection of Relevant Features and Examples in Machine Learning. Artificial Intelligence, 1-2, 245-271.

Boser, B., Guyon, I., & Vapnik, V. (1992). A Training Algorithm for optimal Margin Classifiers. 5th Annual ACM Workshop on COLT, Pittsburgh, PA, ACM Press.

Bradley, A. (1997). The Use of the area under the ROC curve in Evaluation of Machine Learning Algorithms. Pattern Recognition, 30(7), 1145-1159.

Embrechts, M., Szymanski, B., & Sternickel, K. (2004). Introduction to Scientific Data Mining: Direct Kernel Methods and Applications. In S. Ovaska (Ed.), Computationally Intelligent Hybrid Systems: The Fusion of Soft and Hard Computing (pp. 317-362). New York, NY: John Wiley.

Chapelle, O. & Vapnik, V. (2002). Choosing Multiple Parameters for Support Vector Machines. Machine Learning, 46 (1-3), 131-159.

Chapelle, O. & Keerthi, S. (2008). Multi-Class Feature Selection with Support Vector Machines. Proc of American Statistical Association.

Chen, Q., Zhao, J., Chaitep, S., & Guo, Z. (2009). Simultaneous analysis of main catechins contents in green tea (*Camellia sinensis* (L.)) by Fourier transform near infrared reflectance (FT-NIR) spectroscopy. Food Chemistry, 113 (4), 1272-1277.

Cristianini, N. & Campbell, C. (1998). Dynamically Adapting Kernels in Support Vector Machines. Neural Information Processing Systems.

Embrechts, M., Ekins, S. (2007). Classification of metabolites with kernel-partial least squares (K-PLS). Drug Metabolism and Disposition, 35(3), 325-327.

Embrechts, M., Szymanski, B., Sternickel, K., Naenna, T., and Bragaspathi, R. (2003). Use of Machine Learning for Classification of Magnetocardiograms. Proceeding of IEEE Conference on System, Man and Cybernetics, Washington DC.

Embrechts, M., Bress, R., & Kewley, R. (2005). Feature Selection via Sensitivity Analysis with Direct Kernel PLS. In I. Guyon and S. Gunn (Ed.), Feature Extraction. New York, NY: Springer-Verlag.

Fawcett, T. & Provost, F. (2001). Robust Classification for Imprecise Environments. Machine Learning Journal, 42(3), 203-231.

Fawcett, T. (2003). ROC Graphs: Notes and Practical Considerations for Data Mining Researchers. Technical Report HPL-2003-4, Hewlett Packard, Palo Alto, CA.

Fillion, C. & Sharma G. (2010). Detecting Content Adaptive Scaling of Images for Forensic Applications. In N. Memon, J. Dittmann, A. Alattar and E. Delp III (Ed.), Proc. of SPIE-IS&T Electronic Imaging, SPIE vol. 7541.

Grandvalet, Y. & Canu, S. (2002). Adaptive Scaling for Feature Selection in SVMs. Neural Information Processing Systems.

Guo, B., Gunn, S., Damper, R.I., & Nelson, J. (2008) Customizing Kernel Functions for SVM-Based Hyperspectral Image Classification. IEEE Transactions on Image Processing, 17(4), 622-629.

Guyon, I. & Elisseeff, A. (2003). An Introduction to Variable and Feature Selection. Journal of Machine Learning Research, 3, 1157-1182.

Han, L., Embrechts, M., Chen, Y., & Zhang, X. (2006). Kernel Partial Least Squares for Terahertz Radiation Spectral Source Identification. IEEE World Congress on Computational Intelligence.

Han, L., Embrechts, M., Szymanski, B., Sternickel, K., & Ross, A. (2006). Random Forests Feature Selection with K-PLS: Detecting Ischemia from Magnetocardiograms. European Symposium on Artificial Neural Networks, Bruges, Belgium.

He, W., Wang, Z., & Jiang, H. (2008). Model optimizing and feature selecting for support vector regression in time series forecasting. Neurocomputing, 72(1-3), 600-611.

Huang, S., & Wu, T. (2010). Integrating recurrent SOM with wavelet-based kernel partial least squares regressions for financial forecasting. Expert Systems with Applications, 37(8), 5698-5705.

Ilse, C. & Meyer, C. (1998). The Idea behind Krylov Methods. American Mathematical Monthly, 105,889-899.

Kim, K., Kwon, H., Lee, Y. H., Kim, T. E., Kim, J. M., Park Y. K., Moon, J. Y., Ko, Y. G. and Chung, N. (2005). Clinical Parameter Assessment in Magnetocardiography by Using the Support Vector Machine. IJBEM, vol. 7, No. 1.

Lehmann, C., Koenig, T., Jelic, V., Prichep, L., John, R., Wahlund, L., Dodge, Y., & Dierks, T. (2007) Application and comparison of classification algorithms for recognition of Alzheimer's disease in electrical brain activity (EEG). Journal of Neuroscience Method, 161(2), 342-350.

Lindgren, F., Geladi, P., & Wold, S. (1993). The Kernel Algorithm for PLS. Journal of Chemometrics, 7, 45-49.

Liu, S. & Wang, W. (1999). A study on the Applicability on Multicomponent Calibration Methods in Chemometrics. Chemometrics and Intelligent laboratory systems, 45,131-145.

Rosipal, R. and Trejo, L. (2001). Kernel Partial Least Squares Regression in Reproducing Kernel Hillbert Spaces. Journal of Machine Learning Research, 2, 97-128.

Rousseauw, J., du Plessis, J., Benade, A., Jordann, P., Kotze, J., Jooste, P., & Ferreira, J. (1983). Coronary risk factor screening in three rural communities. South African Medical Journal, 64, 430-436.

Rubio, G., Herrera, L., Pomares, H., Rojas, I., & Guillén, A. (2010). Design of Specific-to-problem kernels and use of kernel weighted K-nearest neighbors for time series modeling. Neurocomputing, 73(10-12), 1965-1975.

Specht, D. F. (1990). Probabilistic Neural Networks. Neural Networks, 3, 109-118. Štruc, V., & Pavešić, N. (2009) Gabor-Based Kernel Partial-Least Squares Discrimination for Face Recognition. Informatica, 20, 115-138.

Struc, V. and Pavesic, N. (2009). Gabor-Based Kernel Partial-Least-Squares Discrimination Features for Face Recognition. Informatica, vol. 20, No. 1, 115-138.

Wold, S., Sjölström, M., & Erikson, L. (2001). PLS-Regression: A Basic Tool of Chemometrics. Chemometrics and Intelligent Laboratory Systems, 58, 109-130.

Swets, J., Dawes, R., & Monahan, J. (2000, Oct.). Better Decisions through Science. Scientific American, 82-87.

Szymanski, B., Han, L., Embrechts, M., Ross, A., Sternickel, K., & Zhu, L. (2006). Using Efficient Supanova Kernel for Heart Disease Diagnosis. Proceeding of ANNIE 2006, Intelligent Engineering Systems Through Artificial Neural Networks, St. Louis, MO, ASME, New York, NY.

Tian, H., Tian, X., Deng, X., & Wang, P. (2009). Soft Sensor for Polypropylene Melt Index Based on Adaptive Kernel Partial Least Squares. Control and Instruments in Chemical Industry.

Wang, T., Huang, H., Tian, S., & Xu, J. (2010). Feature selection for SVM via optimization of kernel polarization with Gaussian ARD kernels. Expert Systems with Application, 37(9), 6663-6668.

\* cited by examiner

SIGMA TUNING OF GAUSSIAN KERNELS: DETECTION OF ISCHEMIA FROM MAGNETOCARDIOGRAMS

CROSS REFERENCE TO RELATED APPLICATIONS

This application claims benefit of provisional application U.S. 61/363,915 filed Jul. 13, 2010, which is hereby incorporated by reference. This application is also a continuation-in-part of pending application Ser. No. 12/819,095 filed Jun. 18, 2010. Said Ser. No. 12/819,095 is a continuation of U.S. Ser. No. 10/561,285 filed Dec. 20, 2005, now U.S. Pat. No. 7,742, 806 issued Jun. 22, 2010. Said U.S. Ser. No. 10/561,285 is a US national stage application of PCT/US04/21,307 filed Jul. 1, 2004, which in turn claims benefit of U.S. 60/483,961 filed Jul. 1, 2003. The foregoing are all hereby incorporated by reference.

BACKGROUND OF THE INVENTION

Disclosed herein is a novel tuning mechanism for Gaussian or Radial Basis Function (RBF) kernels where each attribute (or feature) is characterized by its own Parzen window sigma. The kernel trick is frequently used in machine learning to transform the input domain into a feature domain where linear methods are then used to find an optimal solution to a regression or classification problem. Support Vector Machines (SVM), Kernel Principal Component Regression (K-PCR), Kernel Ridge Regression (K-RR), Kernel Partial Least Squares (K-PLS) are examples of techniques that apply kernels for machine learning and data mining. There are many different possible kernels, but the RBF (Gaussian) kernel is one of the most popular ones. Equation (1) represents a single element in the RBF kernel, $$k(i, j) = e^{-\frac{\|x_i - x_j\|^2}{2\sigma^2}} \quad (1)$$

where $x_i$ and $x_j$ denote two sample data. Traditionally, most machine learning approaches use a single value σ in the RBF kernel (as indicated in the equation above), which then needs to be tuned on a validation or tuning data set. Here, each attribute is associated with a different σ value which is then tuned based on a validation data set with the aim to achieve a prediction performance that is an improvement over the one achieved by the RBF kernels with a single σ. The expression for a single RBF kernel entry becomes, $$k(i, j) = \prod_{l=1}^{m} e^{-\frac{\|x_i^l - x_j^l\|^2}{2\sigma_l^2}} \quad (2)$$

where m is the number of attributes in the sample data. There are several advantages of using an automated tuning algorithm for a vector of σ rather than selecting a single scalar variable:

Manual tuning for multiple σ-values is a tedious procedure;
The same automated procedure applies to most machine learning methods that use an RBF kernel;
The values of the optimized a can be used as a gauge for variable selection (Specht, 1990).

Automated tuning of the kernel parameters is an important problem, it could be used in all different scientific applications: such as image classification (Guo, 2008; Claude, 2010) and time series data forecasting (He, 2008; Rubio, 2010), etc. A number of researchers have proposed algorithms for solving it, especially in the context of SVMs. Related work includes Grandvalet et al. (Grandvalet, 2002), which introduced an algorithm for automatic relevance determination of input variables in SVMs. Relevance is measured by scale factors defining the input space metric. The metric is automatically tuned by the minimization of the standard SVM empirical risk, where scale factors are added to the usual set of parameters defining the classifier. Cristianini et al. (Cristianini, 1998) applied an iterative optimization scheme to estimate a single kernel width hyper-parameter in SVM classifiers. In its procedure, model selection and learning are not separate, but kernels are dynamically adjusted during the learning process to find the kernel parameter which provides the best possible upper bound on the generalization error. Chapelle et al. (Chapelle, 2002) extend the single kernel width hyper-parameter to multiple-sigma parameters for solving the same problem in SVMs in order to perform adaptive scaling and variable selection. An example of this method is extended to Gaussian Automatic Relevance Determination kernel via optimization of kernel polarization (Wang, 2010). A further extension includes a multi-Class feature selection in the application of text classification (Chapelle, 2008). Chapelle et al.'s method has the advantage that the gradients are computed analytically as opposed to the empirical approximation used in this paper. The algorithm proposed here is very similar to the one proposed by Chapelle et al. However, the approach here is different in the sense that we use a Levenberg-Marquardt-like optimization approach, which uses a λ parameter that gradually changes the algorithm from a first-order to a second-order. In addition, we use a $Q^2$ error metric which shows more robustness on unbalanced data sets and a leave-several-out validation option for improved computing time. Finally, we apply the algorithm to K-PLS rather than SVMs.

Partial Least Squares (PLS) (H. Wold, 1966) was introduced by Swedish statistician Herman Wold for econometrics modeling of multi-variate time series. Currently PLS has become one of the most popular and powerful tools in chemometrics and drug design after it was applied to chemometrics in the early eighties (S. Wold, 2001). PLS can be viewed as a "better" Principal Components Analysis (PCA) regression method, where the data are first transformed into a different and non-orthogonal basis and only the most important PLS components (or latent variables) are considered for building a regression model (similar to PCA). The difference between PLS and PCA is that the new set of basis vectors in PLS is not a set of successive orthogonal directions that explain the largest variance in the data, but are actually a set of conjugant gradient vectors to the correlation matrix that form a Krylov space (Ilse, 1998), a widely used iterative method for successfully solving large system of linear equations in order to avoid matrix-matrix operations, currently available in numerical linear algebra. PLS regression is one of the most powerful data mining tools for large data sets with many variables with high collinearity. The NIPALS implementation of PLS (H. Wold, 1975) is elegant and fast.

Linear Kernel Partial Least Squares (K-PLS) was first described in (Lindgren, 1993) and applied to spectral analysis in the late nineties of twentieth century (Liu, 1999). Instead of linear K-PLS, Rosipal introduced K-PLS in 2001 (Rosipal, 2001) as a nonlinear extension to the PLS. This nonlinear extension of PLS makes K-PLS a powerful machine learning tool for classification as well as regression. K-PLS can also be formulated as a paradigm closely related to Support Vector Machines (SVM) (Vapnik, 1998; Boser, 1992; Bennett, 2003). In addition, the statistical consistency of K-PLS is recently proved from theoretical perspective (Blanchard, 2010).

Since K-PLS was introduced in 2001, researchers in chemometrics have gradually switched from PLS to K-PLS as a standard tool for the data mining (Embrechts, 2007; Tian, 2009). Meanwhile, K-PLS has been attracted by other researchers for different industrial applications such as face recognition (Štruc, 2009) and financial forecasting (Huang, 2010). In the specific domain (electrocardiogram, echocardiogram, and angiogram, etc.) where signal is retrieved through sensor, machine learning has become a crucial tool for the signal analysis. PLS combining with different signal preprocess techniques are applied in different research projects. Partial least squares logistic regression was used for electroencephalograms for early detection of patients with probable Alzheimer's disease (Lehmann, 2007). Chen et al. (Chen, 2009) conducted partial least squares with Fourier transform in the near infrared reflectance spectroscopy to analyze the main catechins contents in green tea. In this disclosure, a sigma tuning of Gaussian kernel is applied on the magnetocardiogram/graph for the diagnosis of ischemia heart disease. The sigma tuning procedure is implemented for a K-PLS model. The justification here for using K-PLS is that there is generally no significant difference in performance between K-PLS and other kernel-based learning methods such as SVMs (Han, 2006).

For background, the following references are referred to at various points in this application:

Bennett, K. & Embrechts, M. (2003). An Optimization Perspective on Kernel Partial Least Squares Regression. In J. Suykens, G. Horvath, C. M. S. Basu, & J. Vandewalle (Ed.), *Advances in Learning Theory: Methods, Models and Applications*, volume 190 of *NATO Science III: Computer & Systems Sciences* (pp. 227-250). Amsterdam: IOS Press.

Bi, J., Bennett, K., Embrechts, M., Breneman, C., & Song, M. (2003). Dimensionality Reduction via Sparse Support Vector Machines. *Journal of Machine Learning Research*, 3, 1229-1243.

Blanchard, G., & Krämer, N. (2010). Kernel Partial Least Squares is Universally Consistent. Thirteenth International Conference on Artificial Intelligence and Statistics (AISTATS), Sardinia, Italy.

Blum, A. & Langley, P. (1997). Selection of Relevant Features and Examples in Machine Learning. *Artificial Intelligence*, 1-2, 245-271.

Boser, B., Guyon, I., & Vapnik, V. (1992). A Training Algorithm for optimal Margin Classifiers. 5th Annual ACM Workshop on COLT, Pittsburgh, Pa., ACM Press.

Bradley, A. (1997). The Use of the area under the ROC curve in Evaluation of Machine Learning Algorithms. *Pattern Recognition*, 30(7), 1145-1159.

Chang, C. & Lin, C. LIBSVM: A Library for Support Vector Machines. Accessed 5 Sep. 2004, from http://www.csie.ntu.edu.tw/~cjlin/libsvm.

Chapelle, O. & Vapnik, V. (2002). Choosing Multiple Parameters for Support Vector Machines. *Machine Learning*, 46(1-3), 131-159.

Chapelle, O. & Keerthi, S. (2008). Multi-Class Feature Selection with Support Vector Machines. *Proc of American Statistical Association*.

Chen, Q., Zhao, J., Chaitep, S., & Guo, Z. (2009). Simultaneous analysis of main catechins contents in green tea (*Camellia sinensis* (L.)) by Fourier transform near infrared reflectance (FT-NIR) spectroscopy. *Food Chemistry*, 113 (4), 1272-1277.

Cristianini, N. & Campbell, C. (1998). Dynamically Adapting Kernels in Support Vector Machines. Neural Information Processing Systems.

Cristianini, N. & Shawe-Taylor, J. (2000). *Support Vector Machines and Other Kernel based Learning Methods*. Cambridge University Press.

Embrechts, M., Bress, R., & Kewley, R. (2005). Feature Selection via Sensitivity Analysis with Direct Kernel PLS. In I. Guyon and S. Gunn (Ed.), *Feature Extraction*. New York, N.Y.: Springer-Verlag.

Embrechts, M., Szymanski, B., & Sternickel, K. (2004). Introduction to Scientific Data Mining: Direct Kernel Methods and Applications. In S. Ovaska (Ed.), *Computationally Intelligent Hybrid Systems: The Fusion of Soft and Hard Computing* (pp. 317-362). New York, N.Y.: John Wiley.

Embrechts, M., Ekins, S. (2007). Classification of metabolites with kernel-partial least squares (K-PLS). *Drug Metabolism and Disposition*, 35(3), 325-327.

Fawcett, T. (2003). ROC Graphs: Notes and Practical Considerations for Data Mining Researchers. Technical Report HPL-2003-4, Hewlett Packard, Palo Alto, Calif.

Fawcett, T. & Provost, F. (2001). Robust Classification for Imprecise Environments. *Machine Learning Journal*, 42(3), 203-231.

Fillion, C. & Sharma G. (2010). Detecting Content Adaptive Scaling of Images for Forensic Applications. In N. Memon, J. Dittmann, A. Alattar and E. Delp III (Ed.), *Proc. of SPIE-IS&T Electronic Imaging*, SPIE Vol 7541

Golbraikh, A. & Tropsha, A. (2002). Beware of q2!. *Journal of Molecular Graphics and Modeling*, 20, 267-276.

Grandvalet, Y. & Canu, S. (2002). Adaptive Scaling for Feature Selection in SVMs. Neural Information Processing Systems.

Guo, B., Gunn, S., Damper, R. I., & Nelson, J. (2008) Customizing Kernel Functions for SVM-Based Hyperspectral Image Classification. *IEEE TRANSACTIONS ON IMAGE PROCESSING*, 17(4), 622-629.

Guyon, I. & Elisseeff, A. (2003). An Introduction to Variable and Feature Selection. *Journal of Machine Learning Research*, 3, 1157-1182.

Ham, F. & Kostanic, I. (2001). *Principles of Neurocomputing for Science and Engineering*. McGraw Hill.

Han, L., Embrechts, M., Szymanski, B., Sternickel, K., & Ross, A. (2006). Random Forests Feature Selection with K-PLS: Detecting Ischemia from Magnetocardiograms. European Symposium on Artificial Neural Networks, Bruges, Belgium.

Hastie, T., Tibshirani, R., & Friedman, J. (2003). *The Elements of Statistical Learning: Data Mining, Inference, and Prediction*. New York, N.Y.: Springer.

He, W., Wang, Z., & Jiang, H. (2008). Model optimizing and feature selecting for support vector regression in time series forecasting. *Neurocomputing*, 72(1-3), 600-611.

Huang, S., & Wu, T. (2010). Integrating recurrent SOM with wavelet-based kernel partial least squares regressions for financial forecasting. *Expert Systems with Applications*, 37(8), 5698-5705.

Ilse, C. & Meyer, C. (1998). The Idea behind Krylov Methods. *American Mathematical Monthly*, 105, 889-899.

Lehmann, C., Koenig, T., Jelic, V., Prichep, L., John, R., Wahlund, L., Dodge, Y., & Dierks, T. (2007) Application and comparison of classification algorithms for recognition of Alzheimer's disease in electrical brain activity (EEG). *Journal of Neuroscience Method,* 161(2), 342-350.

Lindgren, F., Geladi, P., & Wold, S. (1993). The Kernel Algorithm for PLS. *Journal of Chemometrics,* 7, 45-49.

Liu, S. & Wang, W. (1999). A study on the Applicability on Multicomponent Calibration Methods in Chemometrics. *Chemometrics and Intelligent laboratory systems,* 45, 131-145.

Masters, T. (1995). *Advanced Algorithms for Neural Networks: A C++ Sourcebook.* New York, N.Y.: John Wiley & Sons.

Newman, D., Hettich, S., Blake, C., & Merz, C. (1998). UCI Repository of Machine Learning Databases.

Rosipal, R. and Trejo, L. (2001). Kernel Partial Least Squares Regression in Reproducing Kernel Hillbert Spaces. *Journal of Machine Learning Research,* 2, 97-128.

Rousseauw, J., du Plessis, J., Benade, A., Jordann, P., Kotze, J., Jooste, P., & Ferreira, J. (1983). Coronary risk factor screening in three rural communities. *South African Medical Journal,* 64, 430-436.

Rubio, G., Herrera, L., Pomares, H., Rojas, I., & Guillen, A. (2010). Design of Specific-to-problem kernels and use of kernel weighted K-nearest neighbors for time series modeling. *Neurocomputing,* 73(10-12), 1965-1975.

Specht, D. F. (1990). Probabilistic Neural Networks. *Neural Networks,* 3, 109-118.

Štruc, V., & Pavešić, N. (2009) Gabor-Based Kernel Partial-Least Squares Discrimination for Face Recognition. *Informatica,* 20, 115-138.

Suykens, J., Gestel, T., Brabanter, J., Moor, B., and Vandewalle, J. (2003). *Least Squares Support Vector Machines.* World Scientific Publishing Company.

Swets, J., Dawes, R., & Monahan, J. (2000, October). Better Decisions through Science. *Scientific American,* 82-87.

Tian, H., Tian, X., Deng, X., & Wang, P. (2009). Soft Sensor for Polypropylene Melt Index Based on Adaptive Kernel Partial Least Squares. *Control and Instruments in Chemical Industry.*

Vapnik, V. (1998). *Statistical Learning Theory.* John Wiley & Sons.

Wang, T., Huang, H., Tian, S., & Xu, J. (2010). Feature selection for SVM via optimization of kernel polarization with Gaussian ARD kernels. *Expert Systems with Application,* 37(9), 6663-6668.

Wold, H. (1996). Estimation of Principal Components and related Models by Iterative Least Squares. In P. Krishnaiah (Ed.), *Multivariate Analysis* (pp. 391-420). New York N.Y.: Academic Press.

Wold, H. (1975). Path with Latent Variables: The NIPALS Approach. In H. M. Balock (Ed.), *Quantitative Sociology: International Perspectives on Mathematical and Statistical Model Building* (pp. 307-357). New York N.Y.: Academic Press.

Wold, S., Sjölström, M., & Erikson, L. (2001). PLS-Regression: A Basic Tool of Chemometrics. *Chemometrics and Intelligent Laboratory Systems,* 58, 109-130.

Additional recommended background reading selections include the following:

Bennett, K. & Embrechts, M. (2003). An Optimization Perspective on Kernel Partial Least Squares Regression. In J. Suykens, G. Horvath, C. M. S. Basu, & J. Vandewalle (Ed.), *Advances in Learning Theory: Methods, Models and Applications,* volume 190 of *NATO Science III: Computer & Systems Sciences* (pp. 227-250). Amsterdam: IOS Press.

Chapelle, O. & Vapnik, V. (2002). Choosing Multiple Parameters for Support Vector Machines. *Machine Learning,* 46(1-3), 131-159.

Cristianini, N. & Shawe-Taylor, J. (2000). *Support Vector Machines and Other Kernel based Learning Methods.* Cambridge University Press.

Embrechts, M., Szymanski, B., & Sternickel, K. (2004). Introduction to Scientific Data Mining: Direct Kernel Methods and Applications. In S. Ovaska (Ed.), *Computationally Intelligent Hybrid Systems: The Fusion of Soft and Hard Computing* (pp. 317-362). New York, N.Y.: John Wiley.

Embrechts, M., Bress, R., & Kewley, R. (2005). Feature Selection via Sensitivity Analysis with Direct Kernel PLS. In I. Guyon and S. Gunn (Ed.), *Feature Extraction.* New York, N.Y.: Springer-Verlag.

Han, L., Embrechts, M., Chen, Y., & Zhang, X. (2006). Kernel Partial Least Squares for Terahertz Radiation Spectral Source Identification. IEEE World Congress on Computational Intelligence.

Embrechts, M., Szymanski, B., Sternickel, K., Naenna, T., and Bragaspathi, R. (2003). Use of Machine Learning for Classification of Magnetocardiograms. Proceeding of IEEE Conference on System, Man and Cybernetics, Washington D.C.

Kim, K., Kwon, H., Lee, Y. H., Kim, T. E., Kim, J. M., Park Y. K., Moon, J. Y., Ko, Y. G. and Chung, N. (2005). Clinical Parameter Assessment in Magnetocardiography by Using the Support Vector Machine. IJBEM, Vol. 7, No. 1.

Rosipal, R. & Trejo, L. (2001). Kernel Partial Least Squares Regression in Reproducing Kernel Hilbert Spaces. *Journal of Machine Learning Research,* 2, 97-128.

Schölkopf, B. & Smola, A. (2002). *Learning with Kernels.* MIT Press.

Shawe-Taylor, J. & Cristianini, N. (2004). *Kernel Methods for Pattern Analysis.* Cambridge University Press.

Szymanski, B., Han, L., Embrechts, M., Ross, A., Sternickel, K., & Zhu, L. (2006). Using Efficient SUPANOVA Kernel for Heart Disease Diagnosis. Proceeding of ANNIE 2006, Intelligent Engineering Systems Through Artificial Neural Networks, St. Louis, Mo., ASME, New York, N.Y.

Vapnik, V. (1998). *Statistical Learning Theory.* John Wiley & Sons.

Wold, H. (1975). Path with Latent Variables: The NIPALS Approach. In H. M. Balock (Ed.), *Quantitative Sociology: International Perspectives on Mathematical and Statistical Model Building* (pp. 307-357). New York N.Y.: Academic Press.

Wold, H. (1996). Estimation of Principal Components and related Models by Iterative Least Squares. In P. Krishnaiah (Ed.), *Multivariate Analysis* (pp. 391-420). New York N.Y.: Academic Press.

SUMMARY OF THE INVENTION

Disclosed herein is a novel Levenberg-Marquardt like second-order algorithm for tuning the Parzen window σ in a Radial Basis Function (Gaussian) kernel. In this case each attribute has its own sigma parameter associated with it. The values of the optimized σ are then used as a gauge for variable selection. In this study Kernel Partial Least Squares (K-PLS) model is applied to several benchmark data sets in order to estimate the effectiveness of the second-order sigma tuning procedure for an RBF kernel. The variable subset selection method based on these sigma values is then compared with different feature selection procedures such as random forests and sensitivity analysis. The sigma-tuned RBF kernel model outperforms K-PLS and SVM models with a single sigma value. K-PLS models also compare favorably with Least Squares Support Vector Machines (LS-SVM), epsilon-insensitive Support Vector Regression and traditional PLS. The sigma tuning and variable selection procedure introduced in this paper is applied to industrial magnetocardiogram data for the detection of ischemic heart disease from measurement of the magnetic field around the heart.

Specifically, the invention comprises a method and related apparatus and computer-readable medium for: associating each attribute of a Gaussian or Radial Basis Function data kernel with its own Parzen window sigma, wherein said data kernel is derived from a magnetocardiograph; forming each of said sigmas into an initial vector σ comprising i scalars $\sigma_i$; starting with an initial guess $\sigma_0$ and calculating an initial error metric $E(\sigma_0)=Q_0^2$ from a leave-one-out (or leave-several-out) K-PLS model, with scalar parameter λ=1; a) for each said scalar $\sigma_i$, calculating a corresponding element ΔE in E(σ) by perturbation; b) solving the equation $(H+\lambda I)\Delta\sigma=-\nabla E(\sigma_0)$ for Δσ, where H is a Hessian matrix; c) if $E(\sigma)=Q^2$ has become smaller by virtue of said solution b), updating said σ using said E(σ) and reducing said λ→βλ where β<1, otherwise making no change in said σ and increasing said λ→βλ where β>1; d) if said λ>1, capping λ to λ=1; e) iterating said a) through d) until either said E(σ) can no longer be improved or until a predetermined iteration limit has been reached; and f) replacing said initial vector σ with the updated σ resulting from said e).

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) summarized below.

FIG. 2, right, illustrates relative positions of the heart and the nine sensors (small circles) inside the cryostat housing at four consecutive positions over the body surface.

FIG. 3, upper right, illustrates a spatial map of the cardiac magnetic field generated at an instant within the ST interval.

FIG. 3, lower right, illustrates the T3-T4 sub-cycle in one MCG signal trace.

DETAILED DESCRIPTION

Key Terms & Definitions

Figure 1:
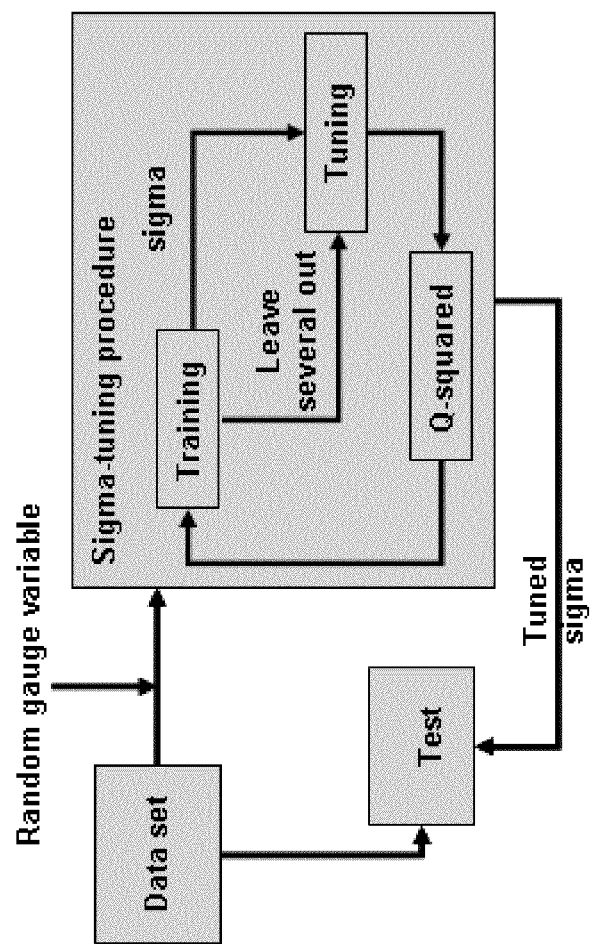
FIG. 1 is a flowchart illustrating the process flow for sigma tuning.
Figure 2:
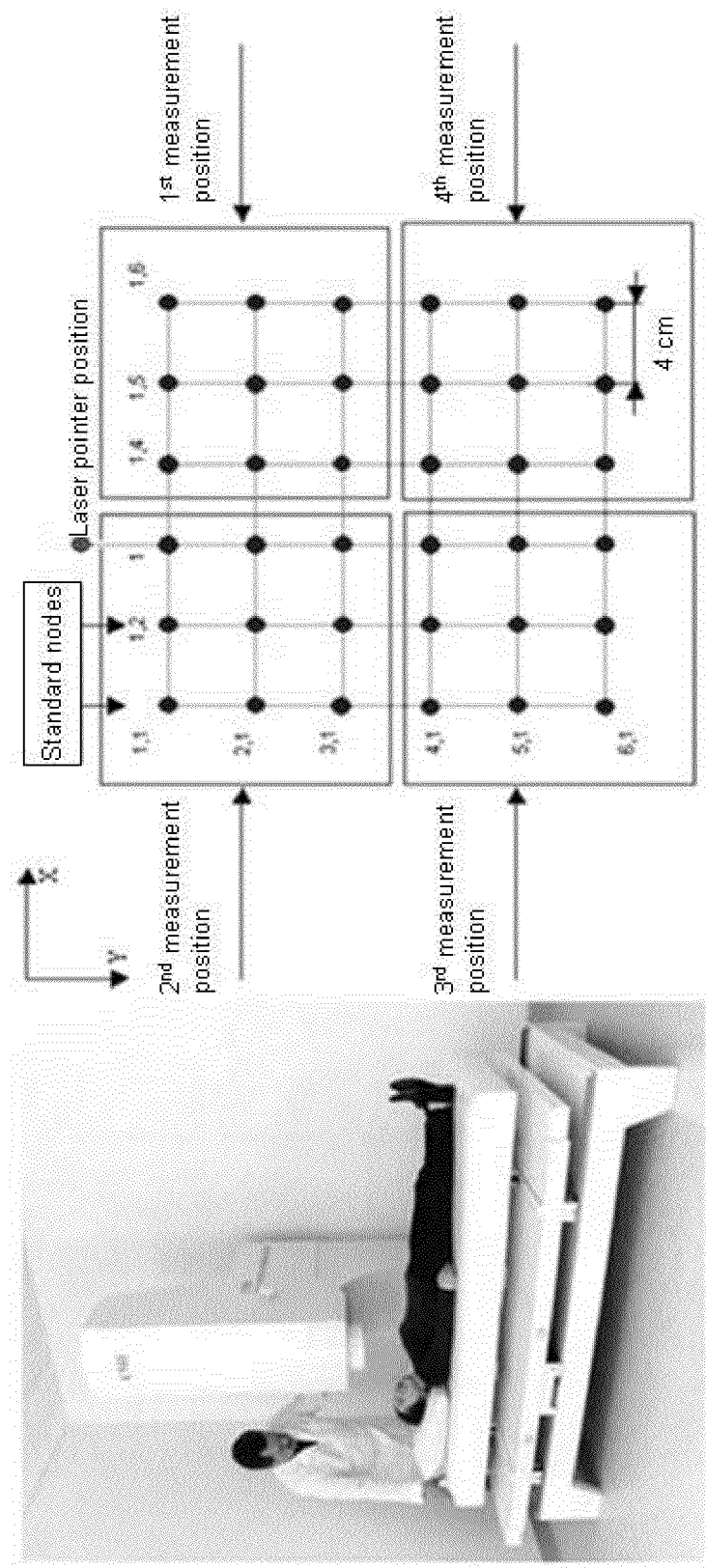
FIG. 2, left, shows the Magnetocardiograph, installed in a hospital room, without magnetic shielding. The figure shows the operator adjusting the subject's position and sensor head level above the torso.

Kernel Partial Least Squares: A kernel function to replace the linear kernel matrices $XX^T$ in the PLS methods. PLS can be viewed as a "better" Principal Components Analysis (PCA) regression method, where the data are first transformed into a different and non-orthogonal basis and only the most important PLS components (or latent variables) are considered for building a regression model.

Gaussian Kernel: or Radial Basic Function (RBF) kernel, is most widely used. Each kernel entry is a dissimilarity measure through using the square of Euclidean distance between two data points in a negative exponential. The σ parameter contained in the entry is the Parzen window width for RBF kernel.

Variable Selection: or feature selection, is a technique in the machine learning or statistics to select a subset of relevant features for building a robust learning model.

Ischemic Heart Disease: mayocardial ischaemia, is a disease caused by reduced blood supply to the heart muscle. It is more common in men and those whose close relatives have ischaemic heart disease.

Levenberg-Marquardt Algorithm: is an algorithm in mathematics and computing to minimize a function by providing a numerical solution. It is a popular alternative to the Gauss-Newton method.

Performance Metrics

A common way to measure error in regression modeling is via the Least Mean Square Error (LMSE), which is defined as the average value of the squared error between predictions for responses and target values according to:

$$LSME = \sqrt{\frac{\sum_{i=1}^{n}(y_i - \hat{y}_i)^2}{n}} \quad (3)$$

where $y_i$ is the response value, $\hat{y}_i$ is its corresponding prediction value, and n is the number of samples. However, the LMSE is dependent on how the response variable is scaled. In order to overcome the scaling effect, two additional metrics are introduced here: $r^2$ and $R^2$. The first metric, $r^2$, is the square of coefficient of correlation between predicted and target values.

$$r^2 = \frac{\left(\sum_{i=1}^{n}(y_i - \hat{\bar{y}})(y_i - \bar{y})\right)^2}{\sum_{i=1}^{n}(y_i - \hat{\bar{y}})^2 \sum_{i=1}^{n}(y_i - \bar{y})^2} \quad (4)$$

Where $\bar{\hat{y}}$ and $\bar{y}$ are mean value for predictions, $\hat{y}$, and target values, y, respectively. $r^2$ is used for assessing the general quality of the trained model. Usually, a higher value for $r^2$ corresponds to a better trained model. An obvious drawback of $r^2$ as an error metric is that $r^2$ only measures a linear correlation, indicating how well the predictions, $\hat{y}$, follow a line if they are plotted as a function of y. While one might expect a nearly perfect model when $r^2$ is close to unity, this is not necessarily the case. For that reason, a second and more powerful error metric will be used: the so-called "Press $R^2$ squared", or $R^2$, which is commonly used in chemometric modeling. $R^2$ is defined as (Embrechts, 2004; Golbraikh, 2002):

$$R^2 = 1 - \frac{\sum_{i=1}^{n}(y_i - \hat{y}_i)^2}{\sum_{i=1}^{n}(y_i - \bar{y})^2} \quad (5)$$

The $R^2$ metric is usually very close to the $r^2$ metric, but is considered a more meaningful error metric than $r^2$ because it accounts for the residual error as well. The higher the value of $R^2$ is, the better is the model. However, it should be noted that in certain cases, the $R^2$ metric can actually become negative. For similar purposes, two related metrics are introduced to assess the performance of validation data or test data: $q^2$ and $Q^2$. They are defined as $1-r^2$ and $1-R^2$, respectively. They are only used in validation and tuning, and only on test data (never on training data).

In addition to the above error metrics, the area under the Receiver Operating Characteristic (ROC) Curve (Swets, 2000; Fawcett, 2001; Fawcett, 2003), AUC (Bradley, 1997), will be used for binary classification problems. The same algorithm will also be applied to regression data for comparative purposes, even though a physical interpretation of the AUC in that case is not obvious. For binary classification problems the balanced error (BE) will also be reported. The balanced error is defined as the average of the correct classification rate between the positive cases and the negative cases.

Sigma Tuning Algorithm

The sigma tuning algorithm will now be explained. Metric $Q^2$ is chosen as an error metric, denoted as $E(\sigma)$, which depends on the vector $\sigma$. Leave-One-Out (LOO) K-PLS is used to obtain an initial $Q_0^2$ value based on an initial starting guess for the sigma-vector denoted as $\sigma_0$. A second-order gradient descent method is utilized to minimize the objective function $E(\sigma)$ and find the optimal choice for $\sigma$. The search process starts from the initial point $E(\sigma_0)=Q_0^2$. The value of $\sigma$ is updated based on the minimization of the leave-one-out (or alternatively, leave several out) tuning (or validation) error, rather than directly minimizing the training error (FIG. 1). According to Newton's rule for finding a minimum in a multi-dimensional space, the relation between $E(\sigma)$ and $\sigma$ at the minimum can be written as:

$$\sigma = \sigma_0 - H^{-1} \nabla E(\sigma_0) \qquad (6)$$

where H is the Hessian matrix. $\nabla E(\sigma_0)$ is a vertical vector, as expressed by:

$$\nabla E(\sigma_0) = \nabla E(\sigma)|_{\sigma=\sigma_0} = \begin{pmatrix} \frac{\partial E}{\partial \sigma_1}|_{\sigma=\sigma_0} \\ \vdots \\ \frac{\partial E}{\partial \sigma_m}|_{\sigma=\sigma_0} \end{pmatrix} \qquad (7)$$

After rearranging, the equation can be reorganized as $$H \Delta \sigma = -\nabla E(\sigma_0) \qquad (8)$$

where $\Delta\sigma = \sigma - \sigma_0$. In order to efficiently proceed towards a converged solution, a Levenberg-Marquardt approach will be utilized. This is achieved by adding a small scalar $\lambda$ to the diagonal elements in the Hessian H, as expressed by:

$$(H+\lambda I)\Delta\sigma = -\nabla E(\sigma_0) \qquad (9)$$

In this approach, the algorithm starts out as a first-order approach and gradually proceeds towards the second-order approach outlined below. We will solve equation (9) for $\Delta\sigma$. Note that each element $$\frac{\partial E}{\partial \sigma_i}\bigg|_{\sigma=\sigma_0}$$

in the right side of equation (7) will be computed by numerical perturbation as shown below:

$$\frac{\partial E}{\partial \sigma_i}\bigg|_{\sigma=\sigma_0} \approx \frac{\Delta E}{\varepsilon}\bigg|_{\sigma=\sigma_0} = \frac{E(\sigma_i + \varepsilon) - E(\sigma_i)}{\varepsilon}\bigg|_{\sigma=\sigma_0} \qquad (10)$$

where $\varepsilon$ is a small perturbation value acting on the $i^{th}$ component in $\sigma$. $E(\sigma_i)$ is the performance metric $Q^2$ obtained from the change in the $i^{th}$ component of $\sigma$ only.

A second approximation will be introduced before solving the above equations. Because the elements of the Hessian are expensive to evaluate, we will introduce a fast and efficient approximation for the Hessian matrix. Each element in the Hessian matrix is originally defined by:

$$H(i,j) = \frac{\partial^2 E}{\partial \sigma_i \partial \sigma_j} \qquad (11)$$

In principal, the second partial derivatives can be numerically calculated. However, in order to speed up the calculation process, the second-order partial derivatives may be approximated by:

$$\frac{\partial^2 E}{\partial \sigma_i \partial \sigma_j} \approx \frac{\partial E}{\partial \sigma_i} \frac{\partial E}{\partial \sigma_j} \qquad (12)$$

This approximation is similar to an approach that is commonly used in the neural network literature (Masters, 1995; Ham, 2001). $\Delta\sigma$ is then solved numerically from equation (9) with a fast conjugate gradient based equation solver in order to avoid calculating the inverse of the Hessian matrix, H (Suykens, 2003). Because of the approximate evaluation of the Hessian, a heuristic coefficient $\alpha$ will be introduced in the iterative updating procedure for the elements of $\sigma$ leading to:

$$\sigma = \alpha \Delta\sigma + \sigma_0$$

The value of $\alpha$ is set to 0.5 which turns out to be a robust choice based on hundreds of experiments with this algorithm on different data sets. A more detailed description for the implementation of the algorithm is shown in FIG. 1 and the sigma tuning algorithm is illustrated in the following:

1. Start with an initial guess $\sigma_0$ and calculate the initial $Q^2$ error metric from a leave-one-out K-PLS model and estimate $E(\sigma_0)$. Start with $\lambda=1$.
2. $\Delta E$ Calculation: For each scalar $\sigma_i$ calculate the corresponding element in $\Delta E$ by perturbation.
3. $\Delta\sigma$ Calculation: Solve equation (9) for $\Delta\sigma$ by using a fast conjugate gradient-based equation solver.
4. $\lambda$ Adjustment: If the $Q^2$ error gets smaller, update $\sigma$ and decrease $\lambda=0.93\lambda$; otherwise, make no change for $\sigma$ and increase $\lambda=3.5\lambda$. If $\lambda>1$, cap $\lambda$ to unity.
5. Iterate the process: Use the new solution as a new starting point and go to step 2. If the error can not be improved (further reduced) or the process reaches the iteration number limit, halt the procedure.

In general, step 4 requires in the adjustment $\lambda \to \beta\lambda$ that if the $Q^2$ error gets smaller, $\beta<1$ and otherwise $\beta>1$. Note that both coefficients $\beta=0.93$ and $\beta=3.5$ are empirical values based on many experiments on different data sets.

Variable Selection

Dimensionality reduction is a challenging problem for supervised and unsupervised machine learning for classification, regression, and time series prediction. In this section we focus on variable selection for supervised classification and regression models. The taxonomy of variable selection has two branches: variable ranking and subset selection (Blum, 1997; Guyon, 2003). Variable subset selection can be further divided into (i) wrappers, (ii) filters, and (iii) embedded methods. The pros and cons of different variable selection methods vary depending on the specific domain problem, computational expense, complexity, and Robustness (Guyon, 2003). In this study, a natural ranking of input variables is proposed based on the values of tuned Parzen window parameters, $\sigma$.

The original variables are ranked corresponding to the sigma ranking (from low to high $\sigma$ values). Bottom-ranked variables, i.e., variables corresponding to a higher $\sigma$ value correspond to features that do not contribute much to the calculation of the RBF kernel entry and are therefore less important. Some of the bottom-ranked variables can therefore be eliminated. The elimination phase can (i) proceed iteratively, where a few variables are dropped at a time, or (ii) proceed in a single-step greedy fashion. A random gauge variable (Embrechts, 2005; Bi, 2003) can be introduced to avoid discarding possibly significant variables. This random variable can either be uniform or Gaussian. Only features that rank below the random gauge variable will be eliminated (during a single step).

After the variable selection stage, a new K-PLS learning model is built based on different bootstraps with bagging in order to evaluate the performance of the sigma tuning based feature selection. Two benchmark data sets illustrate this procedure on a regression and a classification problem. Furthermore, the final predictive models are compared with alternate variable selection procedures based on (i) Random Forests (Han, 2006). Random Forests variable selection with PLS was introduced in (Han, 2006). For each variable subset, a PLS or K-PLS model is used for training and validation. For each variable, a score is based on the $Q^2$ metric for the model in which this variable participated. Finally, variables are ranked according to the average score of each feature. (ii) Sensitivity Analysis (Embrechts, 2005). The hypothesis of Sensitivity Analysis is that variables that change the output more when tweaked are more sensitive and therefore more important. Sensitivity Analysis can easily be implemented as follows: once a model is built, all features are frozen at their average values, and then, one-by-one, the features are tweaked within their allowable range. The features for which the predictions do not vary a lot when they are tweaked are considered less important, and they are slowly pruned out from the input data in a set of Successive iterations between model building and feature selection (Embrechts, 2005). (iii) A simple linear kernel PLS model with Z-scores. Z-scores are a linear statistical method for selecting the important variables in a regression or classification problem (Hastie, 2003).

Experimental Results/Benchmark Data

Sigma tuning based variable selection with K-PLS was benchmarked with two data sets: South African Heart Data (SAheart) and the Boston housing market data. The SAheart is a subset from a larger data set (Rousseauw, 1983) which defines an almost linear classification problem. It describes a retrospective sample of males in a high-risk heart-disease region of the Western Cape in South Africa. There are roughly two controls per case of Coronary Heart Disease (CHD). It consists of one response and nine variables: systolic blood pressure (sbp), cumulative tobacco consumption (tobacco), low density lipoprotein cholesterol level (ldl), adiposity, family history of heart disease (famhist), type-A behavior (typea), obesity, alcohol, and age. A total of 462 samples are included in this data set.

The Boston housing data is a standard benchmark regression data set from the UCI data Repository for Machine Learning (Merz, 1998). This benchmark data set has 506 samples with 12 continuous and one binary variable: per capita crime rate (CRIM), proportion of residential land zoned (ZN), proportion of non-retail business acres (INDUS), Charles River dummy variable (CHAS), nitric oxides concentration (NOX), average number of rooms (RM), proportion of owner-occupied units (AGE), weighted distances (DIS), index of accessibility (RAD), full-value property-tax rate (TAX), pupil-teacher ratio (PTRATIO), B value (B) and a percentage of population with low status (LSTAT) and one response variable: median value of owner-occupied homes (MEDV) in $1000 and capped at $50,000.

TABLE 1

Experimental results with all variables

| Data sets | q2 | $Q^2$ | AUC | LMSE | BE | Comments |
|---|---|---|---|---|---|---|
| Boston ($\sigma$ Kernel-PLS) | 0.127* | 0.133* | — | 3.882 | — | LVs = 12 |
| Boston (K-PLS) | 0.129 | 0.135 | — | 3.904 | — | LVs = 12, $\sigma$ = 4 |
| Boston (LS-SVM) | 0.129 | 0.134 | — | 3.811 | — | $\sigma$ = 4 |
| Boston ($\epsilon$-SVR) | 0.133 | 0.135 | — | 3.903 | — | $\sigma$ = 4 |
| Boston (PLS) | 0.260 | 0.278 | — | 5.607 | — | — |
| SAheart ($\sigma$ Kernel-PLS) | 0.750 | 0.756 | 0.797 | 0.422 | 67.8 | LVs = 3 |
| SAheart (K-PLS) | 0.760 | 0.766 | 0.790 | 0.426 | 68.8 | LVs = 5, $\sigma$ = 30 |
| SAheart (LS-SVM) | 0.730* | 0.748* | 0.812 | 0.421 | 68.8 | $\sigma$ = 30 |
| SAheart ($\epsilon$-SVR) | 0.750 | 0.834 | 0.794 | 0.445 | 71.4 | $\sigma$ = 30 |
| SAheart (PLS) | 0.749 | 0.755 | 0.797 | 0.423 | 67.9 | $\sigma$ = 30 |

Notes: The * indicates the best performance

For each data set, 350 instances are randomly selected for training data, the remaining data are used as test data. We use normalization scaling to pre-process the data for both data sets.

During the sigma tuning stage, a leave-several-out K-PLS model with (tuned) 5 Latent Variables (LVs) was evaluated to calculate a $Q^2$-error metric from the training data. For both benchmark data sets, 70 data instances were randomly selected for a single leave-several-out validation case. 200 sigma tuning iterations were sufficient for a stable set of $\sigma$ values. The starting value for $\sigma_0$ for the Boston Housing data is initialized to 2, a relatively low value. For the South Africa Heart, the initial value for $\sigma$ is set to 30, because this data set is known to lead to linear machine learning models.

TABLE 2

Experimental results with reduced set of variables

| Data sets | q2 | $Q^2$ | AUC | LMSE | BE | Comments |
|---|---|---|---|---|---|---|
| Boston ($\sigma$ Tuning) | 0.131* | 0.136* | — | 3.927 | — | "crim", "chas" |
| Boston (RF) | 0.134 | 0.142 | — | 4.008 | — | "zn", "age" |
| Boston (Z-scores) | 0.138 | 0.146 | — | 4.071 | — | "age", "indus" |
| Boston (SA) | 0.133 | 0.138 | — | 3.900 | — | "zn", "indus" |
| SAheart ($\sigma$ Tuning) | 0.714* | 0.721* | 0.810 | 0.413 | 69.6 | "obesity", "alcohol" |
| SAheart (RF) | 0.762 | 0.768 | 0.793 | 0.426 | 69.6 | "sbp", "alcohol" |
| SAheart (Z-scores) | 0.762 | 0.768 | 0.793 | 0.426 | 69.6 | "sbp", "alcohol" |
| SAheart (SA) | 0.785 | 0.793 | 0.770 | 0.433 | 68.8 | "sb", "ldl" |

Notes: The * indicates the best performance

Before comparing different variable selection methods on the benchmark data, the results of a sigma-tuned K-PLS model are compared with those obtained from other machine learning methods include (i) Least Squares Support Vector Machines (LS-SVM), (ii) ε-insensitive Support Vector Regression (Chang, 2004) (ε-SVR), and (iii) PLS. The prediction results shown in Table 2 indicate that sigma-tuned K-PLS outperforms K-PLS with a single sigma value. The K-PLS results also outperform or are close to the other machine learning models. For the metrics presented in this table, the models were built by bagging all the models obtained from a leave-one-out training procedure.

For the variable selection based on sigma tuning, two criteria are used. One criterion is based on rejecting variables that correspond to larger σ; the second criterion aims to retain at least a similar performance metric between models with all the variables and models with a reduced set of variables. Based on the relative variable importance metric for the SAheart data, the variables "alcohol" and "obesity" were dropped from these data. Likewise, two variables, "CRIM" and "CHAS", are discarded from the original variables in the Boston housing data. Furthermore, when we continue to dropping the third variable, "ZN", the model with the remaining variables still maintains a similar prediction performance (Table 2). Note that for both data sets only a few features are eliminated in order to maintain a prediction performance similar to the models without variable selection.

The results of variable reduction for both benchmark data sets are shown in Table 2. Notice that the σ-tuning based feature selection results are better than the results obtained from the other two feature selection methods. Note also that by using leave-one-out modeling, the performance metrics have a low variance.

Classification of Magnetocardiograms

Figure 3:
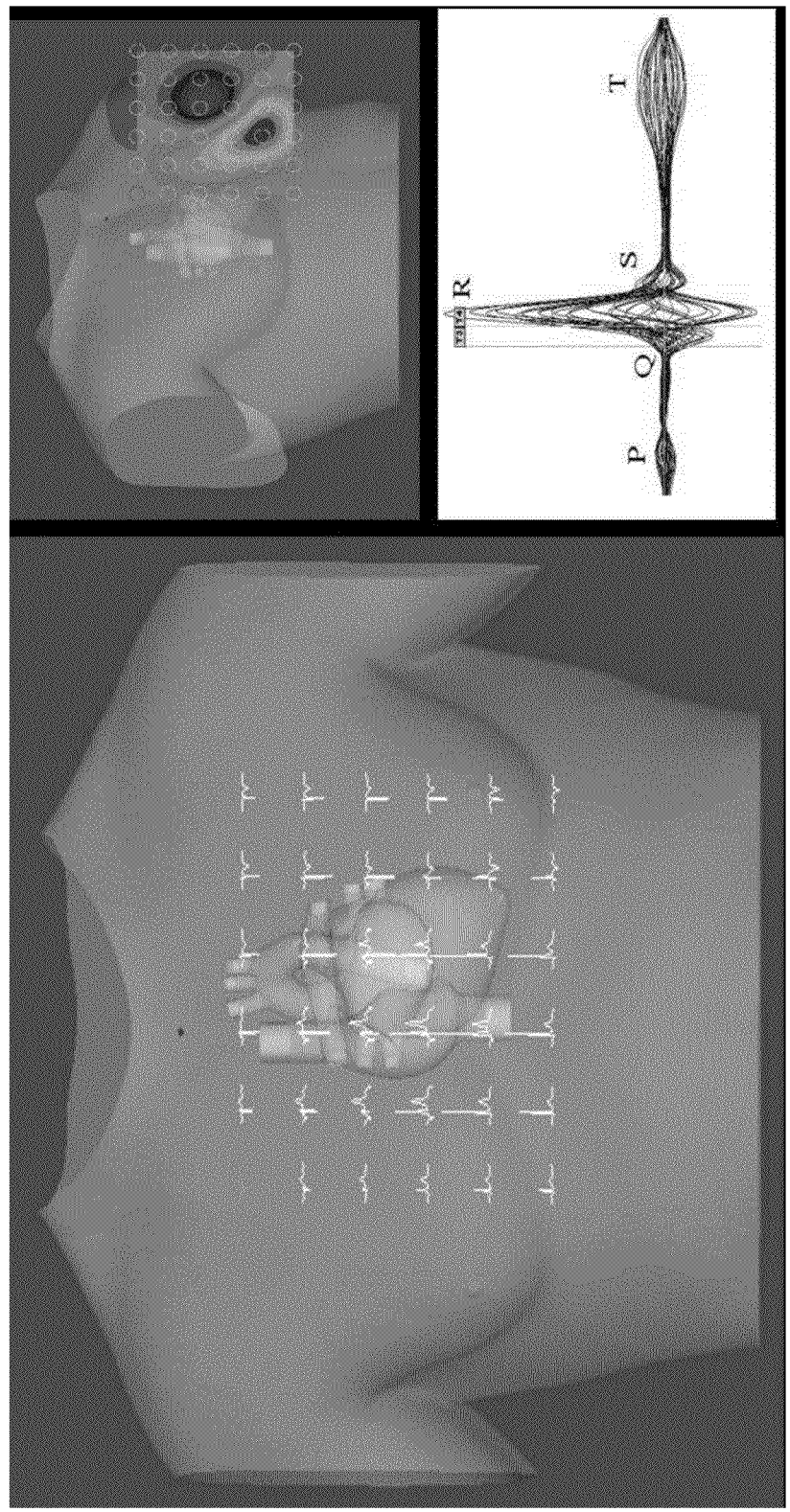
FIG. 3, left, illustrates filtered and averaged temporal MCG Trace for one cardiac cycle in 36 channels (the 6×6 grid).

The aim of Magnetocardiogram (MCG) based cardiology is to rapidly identify and localize the onset of heart disease from measuring the magnetic field of the heart. In this application we are interested in detecting myocardial ischemia, i.e., a cardiac condition in which there is a restriction in blood supply to the heart. FIG. 3 illustrates an MCG system (Model CMI-2049, CardioMag Imaging, Inc., Schenectady, N.Y.) which collects cardiac magnetic field data at 36 points spread over the torso in four sequential measurements in mutually adjacent positions. Data acquisition at 1 kHz for 90 seconds per position results in 36 individual time series of 90,000 samples each. These data are filtered and averaged to produce average cardiac cycles at each of the 36 measurement points. Additional post-processing of the T-wave portion the average cardiac cycles yield a set of 74 variables. The 74 variables are related to delay behaviors of the individual signal traces in the T3-T4 region. 325 patients sample data were collected for the automated detection of ischemic heart disease. There are two response classes: negative and positive.

The MCG data are normalized and 241 instances are randomly selected as training data; the remaining 84 samples are used as test data.

For MCG data, five Latent Variables (LVs) were used. Deleted variables are listed in the last column of Table 4. Table 4 shows that Random Forests results outperform Z-scores ranking and they are close to those obtained from Sensitivity Analysis.

In this study, two experiments were conducted for these data that utilize the sigma tuning algorithm introduced in this study. In one case, three sets of variables are associated with three different Parzen window σ's, because each variable in one of these three sets has a very similar physical meaning. In the other case, each of the 74 variables is characterized by a different Parzen window σ. The sigma tuning procedure is carried with 5 latent variables out in a leave-several-out model, where 50 data are left out from 241 with 120 iterations. The starting value for $\sigma_0$ is initialized to 2 as well.

TABLE 3

Experimental results for MCG data with all variables

| Data sets | q2 | $Q^2$ | AUC | LMSE | BE | Comments |
|---|---|---|---|---|---|---|
| MCG (σ Kernel-PLS) | 0.542* | 0.560* | 0.884 | 0.743 | 81.0 | LVs = 5 |
| MCG (σ Kernel-PLS) | 0.617 | 0.623 | 0.856 | 0.785 | 81.7 | LVs = 5, group σ |
| MCG (K-PLS) | 0.595 | 0.611 | 0.855 | 0.776 | 82.5 | LVs = 5, σ = 4 |
| MCG (LS-SVM) | 0.607 | 0.622 | 0.845 | 0.783 | 82.5 | σ = 4 |
| MCG (ε-SVR) | 0.626 | 0.651 | 0.838 | 0.801 | 81.7 | σ = 4 |
| MCG (PLS) | 0.805 | 0.957 | 0.761 | 0.972 | 73.3 | — |

Notes: The * indicates the best performance

TABLE 4

Experimental results for MCG data with reduced set of variables

| Data sets | q2 | $Q^2$ | AUC | LMSE | BE | Comments |
|---|---|---|---|---|---|---|
| MCG (σ Tuning) | 0.551* | 0.565* | 0.880 | 0.747 | 80.7 | 7 vars deleted |
| MCG (RF) | 0.611 | 0.621 | 0.852 | 0.782 | 81.7 | 7 vars deleted |
| MCG (Z-scores) | 0.627 | 0.637 | 0.848 | 0.793 | 78.3 | 7 vars deleted |
| MCG (SA) | 0.592 | 0.604 | 0.859 | 0.772 | 83.3 | 7 vars deleted |

Notes: The * indicates the best performance

Figure 4:
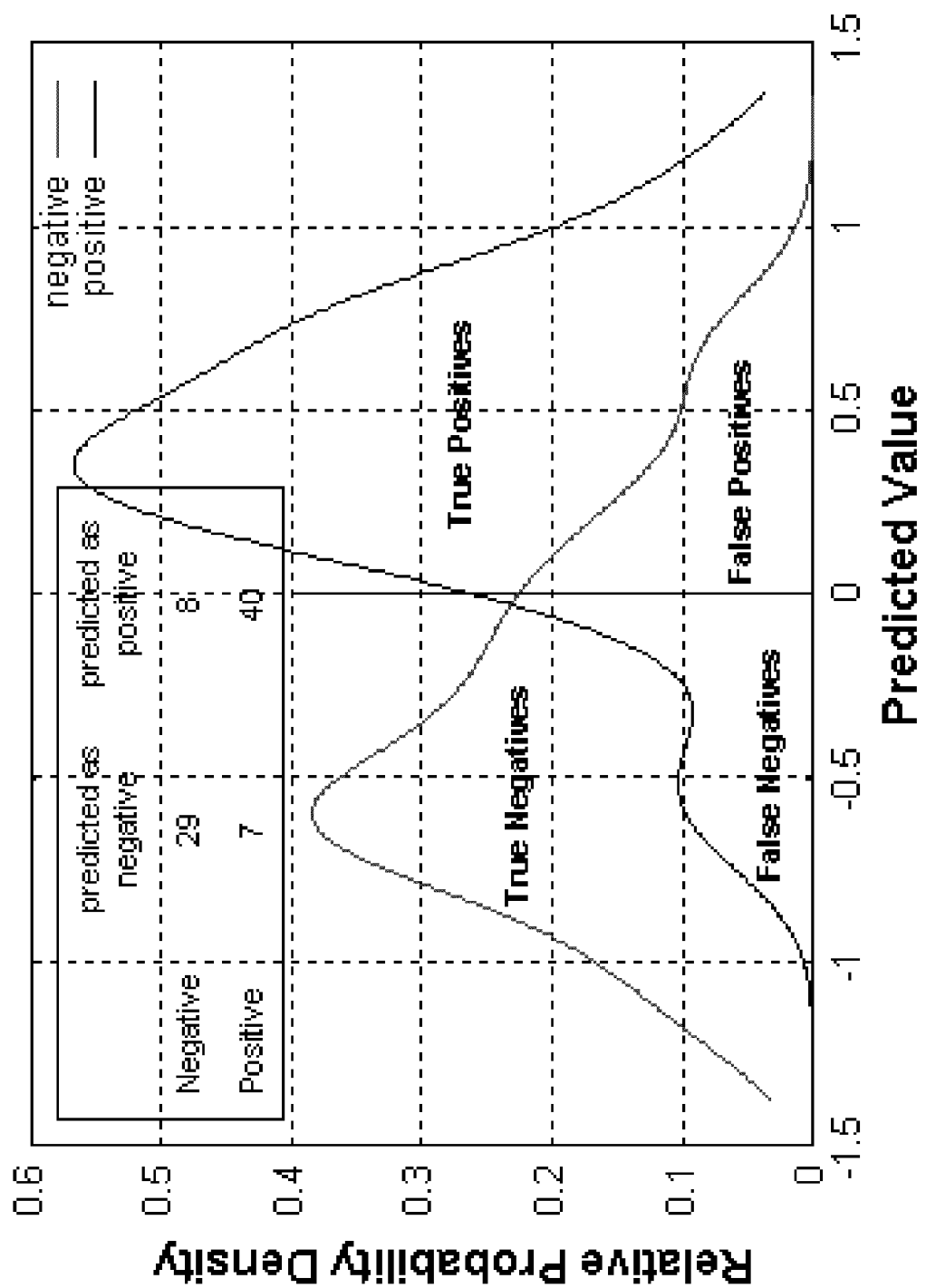
FIG. 4 is a graph illustrating prediction results for the MCG data set with relative probability densities for the positive and negative classes.

For the experiment with three group σ's, the results illustrate a stable convergence of the sigma tuning algorithm. The last two features (#73 and #74) can be discarded from the model because of their large σ value. After discarding these two features, we still obtain undiminished prediction performance. 200 iterations are used for the second case experiment. Experimental results indicate that the variable ranking is relatively robust over the number of iterations. In the final model, as shown in Table 4, the seven variables with the highest σ values are discarded, maintaining a similar $Q^2$ and $q^2$ performance as for the original 74 variable model. The final predictions for the test data are shown in FIG. 4. Two probability density functions are generated based on the prediction results for each class. Note that the balance error depends on the setting of threshold. The threshold value for the results shown in FIG. 4 is set at zero. The corresponding confusion matrix is also illustrated in FIG. 4.

Future Research Direction

The sigma tuning procedure outlined in this disclosure could only proceed in a timely matter by introducing a heuristic approximation for the second-order derivatives in the Hessian matrix. Further research will compare this approach with a more accurate way of calculating the second-order derivatives based on a numerical perturbation approach. Further research is also needed to assess whether the Mercer condition (Cristianini, 2000) is satisfied with the sigma-tuned kernels used in this chapter. Of course, we can always consider the revised kernel function as a data transformation technique similar to DK-PLS (Bennett, 2003) and then still apply K-PLS. In extension to the current implementation of single response, a multiple response sigma tuning algorithm can be investigated for the future work.

In the application of the MCG data analysis, we realized the bias in the samples, where the number of patients having positive is less than the number of patients having negative.

Using the current objective function in the K-PLS will put less weight on negative samples and lead to bias in the model calibration. It would be better to use a different loss function rather than quadratic loss to catch the bias in the samples. A further research is to generalize K-PLS so that it can be applied to all different loss functions, including entropy loss function for the biased samples.

CONCLUSION

We introduced a novel Levenberg-Marquardt like second-order algorithm for tuning the Parzen window sigmas in a RBF kernel. The effectiveness of this algorithm was demonstrated with K-PLS. After tuning the sigmas, we then introduced a novel variable selection procedure by (iteratively) discarding variables with larger associated sigmas. Benchmark comparisons showed the effectiveness of the tuning procedure and the sigma tuning based variable selection method.

The knowledge possessed by someone of ordinary skill in the art at the time of this disclosure is understood to be part and parcel of this disclosure and is implicitly incorporated by reference herein, even if in the interest of economy express statements about the specific knowledge understood to be possessed by someone of ordinary skill are omitted from this disclosure. While reference may be made in this disclosure to the invention comprising a combination of a plurality of elements, it is also understood that this invention is regarded to comprise combinations which omit or exclude one or more of such elements, even if this omission or exclusion of an element or elements is not expressly stated herein, unless it is expressly stated herein that an element is essential to applicant's combination and cannot be omitted. It is further understood that the related prior art may include elements from which this invention may be distinguished by negative claim limitations, even without any express statement of such negative limitations herein. It is to be understood, between the positive statements of applicant's invention expressly stated herein, and the prior art and knowledge of the prior art by those of ordinary skill which is incorporated herein even if not expressly reproduced here for reasons of economy, that any and all such negative claim limitations supported by the prior art are also considered to be within the scope of this disclosure and its associated claims, even absent any express statement herein about any particular negative claim limitations.

Finally, while only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

We claim:

1. A method for improving the detection of ischemia from magnetocardiographs, using computerized devices comprising means for storing and processing data, said method comprising:
    associating each attribute of a Gaussian or Radial Basis Function data kernel with its own Parzen window sigma, wherein said data kernel is derived from a magnetocardiograph;
    forming each of said sigmas into an initial vector $\sigma$ comprising i scalars $\sigma_i$;
    starting with an initial guess $\sigma_0$ and calculating an initial error metric $E(\sigma_0)=Q_0^2$ from a leave-one-out (or leave-several-out) K-PLS model, with scalar parameter $\lambda=1$;
    a) for each said scalar $\sigma_i$, calculating a corresponding element $\Delta E$ in $E(\sigma)$ by perturbation;
    b) solving the equation $(H+\lambda I)\Delta\sigma=-\nabla E(\sigma_0)$ for $\Delta\sigma$, where H is a Hessian matrix;
    c) if $E(\sigma)=Q^2$ has become smaller by virtue of said solution b), updating said $\sigma$ using said $E(\sigma)$ and reducing said $\lambda\rightarrow\beta\lambda$ where $\beta<1$, otherwise making no change in said $\sigma$ and increasing said $\lambda\rightarrow\beta\lambda$ where $\beta>1$;
    d) if said $\lambda>1$, capping $\lambda$ to $\lambda=1$;
    e) iterating said a) through d) until either said $E(\sigma)$ can no longer be improved or until a predetermined iteration limit has been reached; and
    f) replacing said initial vector $\sigma$ with the updated $\sigma$ resulting from said e).

2. The method of claim 1, wherein said $\beta=0.93$ when said $E(\sigma)=Q^2$ has become smaller by virtue of said solution b).

3. The method of claim 1, wherein said $\beta=3.5$ when said $E(\sigma)=Q^2$ has not become smaller by virtue of said solution b).

4. An apparatus for improving the detection of ischemia from magnetocardiographs, comprising computerized storage and processing capacity for:
    associating each attribute of a Gaussian or Radial Basis Function data kernel with its own Parzen window sigma, wherein said data kernel is derived from a magnetocardiograph;
    forming each of said sigmas into an initial vector $\sigma$ comprising i scalars $\sigma_i$;
    starting with an initial guess $\sigma_0$ and calculating an initial error metric $E(\sigma_0)=Q_0^2$ from a leave-one-out (or leave-several-out) K-PLS model, with scalar parameter $\lambda=1$;
    a) for each said scalar $\sigma_i$, calculating a corresponding element $\Delta E$ in $E(\sigma)$ by perturbation;
    b) solving the equation $(H+\lambda I)\Delta\sigma=-\nabla E(\sigma_0)$ for $\Delta\sigma$, where H is a Hessian matrix;
    c) if $E(\sigma)=Q^2$ has become smaller by virtue of said solution b), updating said $\sigma$ using said $E(\sigma)$ and reducing said $\lambda\rightarrow\beta\lambda$ where $\beta<1$, otherwise making no change in said $\sigma$ and increasing said $\lambda\rightarrow\beta\lambda$ where $\beta>1$;
    d) if said $\lambda>1$, capping $\lambda$ to $\lambda=1$;
    e) iterating said a) through d) until either said $E(\sigma)$ can no longer be improved or until a predetermined iteration limit has been reached; and
    f) replacing said initial vector $\sigma$ with the updated $\sigma$ resulting from said e).

5. The apparatus of claim 4, wherein said $\beta=0.93$ when said $E(\sigma)=Q^2$ has become smaller by virtue of said solution b).

6. The apparatus of claim 4, wherein said $\beta=3.5$ when said $E(\sigma)=Q^2$ has not become smaller by virtue of said solution b).

7. A non-transitory computer-readable medium for improving the detection of ischemia from magnetocardiographs, comprising a set of instructions executable by a computerized system for:
    associating each attribute of a Gaussian or Radial Basis Function data kernel with its own Parzen window sigma, wherein said data kernel is derived from a magnetocardiograph;
    forming each of said sigmas into an initial vector $\sigma$ comprising i scalars $\sigma_i$;
    starting with an initial guess $\sigma_0$ and calculating an initial error metric $E(\sigma_0)=Q_0^2$ from a leave-one-out (or leave-several-out) K-PLS model, with scalar parameter $\lambda=1$;
    a) for each said scalar $\sigma_i$, calculating a corresponding element $\Delta E$ in $E(\sigma)$ by perturbation;
    b) solving the equation $(H+\lambda I)\Delta\sigma=-\nabla E(\sigma_0)$ for $\Delta\sigma$, where H is a Hessian matrix;
    c) if $E(\sigma)=Q^2$ has become smaller by virtue of said solution b), updating said $\sigma$ using said $E(\sigma)$ and reducing said $\lambda\rightarrow\beta\lambda$ where $\beta<1$, otherwise making no change in said $\sigma$ and increasing said $\lambda\rightarrow\beta\lambda$ where $\beta>1$;

d) if said $\lambda > 1$, capping $\lambda$ to $\lambda = 1$;

e) iterating said a) through d) until either said $E(\sigma)$ can no longer be improved or until a predetermined iteration limit has been reached; and f) replacing said initial vector $\sigma$ with the updated $\sigma$ resulting from said e).

8. The computer-readable medium of claim 7, wherein said $\beta = 0.93$ when said $E(\sigma) = Q^2$ has become smaller by virtue of said solution b).

9. The computer-readable medium of claim 7, wherein said $\beta = 3.5$ when said $E(\sigma) = Q^2$ has not become smaller by virtue of said solution b).

* * * * *